(12) United States Patent
Makino et al.

(10) Patent No.: US 7,488,498 B2
(45) Date of Patent: *Feb. 10, 2009

(54) ANTIDIABETIC PREPARATION FOR ORAL ADMINISTRATION

(75) Inventors: Chisato Makino, Kawasaki (JP); Nobutaka Ninomiya, Kawasaki (JP); Haruo Orita, Kawasaki (JP); Hidetoshi Sakai, Kawasaki (JP); Akira Yabuki, Kawasaki (JP); Nobuo Kato, Tokyo (JP); Shigeru Shioya, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/246,453

(22) Filed: Oct. 11, 2005

(65) Prior Publication Data

US 2006/0029669 A1  Feb. 9, 2006

Related U.S. Application Data

(63) Continuation of application No. 10/183,322, filed on Jun. 28, 2002, now Pat. No. 7,022,339, which is a continuation of application No. PCT/JP00/09281, filed on Dec. 27, 2000.

(30) Foreign Application Priority Data

Dec. 28, 1999 (JP) ............................... 11-374959
Mar. 24, 2000 (JP) ............................. 2000-085159

(51) Int. Cl.
*A61K 9/14* (2006.01)
*A61K 9/20* (2006.01)
*A61K 9/22* (2006.01)
*A61K 9/24* (2006.01)
*A61K 9/36* (2006.01)

(52) U.S. Cl. ...................... 424/472; 424/464; 424/465; 424/468; 424/469; 424/484

(58) Field of Classification Search ....................... None
See application file for complete search history.

(56) References Cited

U.S. PATENT DOCUMENTS

| | | | |
|---|---|---|---|
| 5,296,236 A | | 3/1994 | Santus et al. |
| 5,609,884 A | | 3/1997 | Desai |
| 6,004,582 A | * | 12/1999 | Faour et al. ................. 424/473 |
| 6,056,977 A | * | 5/2000 | Bhagwat et al. ............. 424/488 |
| 6,143,323 A | * | 11/2000 | Yabuki et al. ................ 424/464 |
| 6,197,348 B1 | * | 3/2001 | Morella et al. .............. 424/497 |
| 6,296,872 B1 | | 10/2001 | Yabuki et al. |
| 6,414,126 B1 | * | 7/2002 | Ellsworth et al. .......... 536/17.2 |
| 6,559,188 B1 | | 5/2003 | Gatlin et al. |
| 6,638,535 B2 | | 10/2003 | Lemmens et al. |
| 6,641,841 B2 | | 11/2003 | Yabuki et al. |
| 6,830,759 B2 | | 12/2004 | Makino et al. |
| 6,844,008 B2 | | 1/2005 | Yabuki et al. |
| 7,022,339 B2 | | 4/2006 | Makino et al. |
| 2003/0077297 A1 | * | 4/2003 | Chen et al. .................. 424/400 |
| 2003/0124191 A1 | | 7/2003 | Besse et al. |
| 2004/0014815 A1 | | 1/2004 | Ninomiya et al. |
| 2004/0029968 A1 | | 2/2004 | Ninomiya et al. |
| 2006/0029669 A1 | | 2/2006 | Makino et al. |

FOREIGN PATENT DOCUMENTS

| | | |
|---|---|---|
| EP | 0 793 959 | 9/1997 |
| EP | 0 965 339 | 12/1999 |
| JP | 10-231242 | 9/1998 |
| JP | 11-130696 | 5/1999 |
| JP | 11-139960 | 5/1999 |
| JP | 2001-2583 | 1/2001 |
| WO | WO 94/05277 | 3/1994 |
| WO | WO 98/02105 | 1/1998 |
| WO | WO 98/56378 | 12/1998 |
| WO | WO 01/21159 | 3/2001 |
| WO | WO 01/47557 | 7/2001 |

OTHER PUBLICATIONS

Journal of Clinical and Experimental Medicine, Jan. 30, 1999, vol. 188, No. 5, pp. 518-521.
Starlix, , Novartis Package Insert, DJN 608/Nateglinide, Jan. 4, 2001, pp. 1-12.
Doctors Guide Global Edition, FDA Approves Starlix (Nateglinide) for Type Diabetes, Dec. 27, 2000, pp. 1-3.
Diabetes Center, Department of Internal Medicine, University of Munich, Germany, Record 7, Meglitinide analogues in the treatment of type 2 diabetes mellitus, (Abstract) Drugs Aging, vol. 17, Issue 5.
Web address: http//www.home.eznet.net/~webtent/repaglinide. html, Repaglinide (Prandin), printed on Jun. 24, 2002.
Carol Lewis, Diabetes: A Growing Public Health Concern, U.S. Food and Drug Administration, FDA Consumer Magazine, Jan.-Feb. 2002.
U.S. Food and Drug Administration, FDA Consumer Magazine, Oral Antidiabetes Medications, Jan.-Feb. 2002.
A. Bakkali-Nadi, et al., "Insulinotroopic Action of Meglitinide Analogs: Concentration-Response Relationship and Nutrient Dependency", Diabetes Research, 1994, 27, pp. 81-87.
B. Luna, et al., "Oral Agents in the Management of Type 2 Diabetes Mellitus", American Family Physician, May 1, 2001, vol. 63, No. 9, pp. 1747-1756.
U.S. Appl. No. 11/349,225, filed Feb. 8, 2006, Makino et al.
U.S. Appl. No. 11/246,453, filed Oct. 11, 2005, Makino et al.

\* cited by examiner

*Primary Examiner*—S. Tran
(74) *Attorney, Agent, or Firm*—Oblon, Spivak, McClelland, Maier & Neustadt, P.C.

(57) ABSTRACT

There is provided a single preparation which directly decreases both of the post prandial blood glucose level and the fasting blood glucose level close to normal levels, by release-sustaining a drug capable of decreasing the post prandial blood glucose level of diabetic patients close to the normal level, or mixing a controlled release drug capable of decreasing the post prandial blood glucose level close to the normal level with an immediate release drug. It is particularly preferable that the drug capable of decreasing the post prandial blood glucose level close to the normal level is nateglinide.

57 Claims, 10 Drawing Sheets

ANTIDIABETIC PREPARATION FOR ORAL ADMINISTRATION

CONTINUING APPLICATION DATA

The present application is a Continuation of prior U.S. Application Ser. No. 10/183,322, filed Jun. 28, 2002, pending, which is a Continuation of International Application serial No. PCT/JP00/09281, filed on Dec. 27, 2000.

BACKGROUND OF THE INVENTION

The present invention relates to an antidiabetic, particularly to a preparation for directly controlling, namely decreasing both a post prandial blood glucose level and a fasting blood glucose level of diabetic patients with one preparation to make these levels close to normal levels.

Ordinary antidiabetics are antidiabetics for decreasing either a post prandial blood glucose level or a fasting blood glucose level to make it close to a normal level. As antidiabetics for decreasing a post prandial blood glucose level to make it close to a normal level, nateglinide has been developed, and it is described in, for example, Japanese Patent Publication No. 15,221/1992 or Japanese Patent Laid-Open No. 194,969/1998. Further, antidiabetics for decreasing a fasting blood glucose level to make it close to a normal level are described in, for example, Kondo Nobuo, Nippon Rinsho, vol. 55, 1997, extra ed., p. 159 and the like. In recent years, for treating diabetes, it has been considered important that both a post prandial blood glucose level and a fasting blood glucose level are decreased to make them close to normal levels.

However, there have been no preparations for decreasing both levels to make them close to normal levels.

DISCLOSURE OF THE INVENTION

The invention is to provide a preparation for directly decreasing both a post prandial blood glucose level and a fasting blood glucose level by one preparation to make them close to normal levels.

The present inventors have assiduously conducted investigations to solve the foregoing problems, and have consequently found that both a post prandial blood glucose level and a fasting blood glucose level can be decreased by one preparation to make them close to normal levels. This finding has led to the completion of the invention.

That is, the invention provides an antidiabetic preparation for oral administration characterized by containing active ingredient(s) for decreasing blood glucose level of diabetic patients and having a form to make both a post prandial blood glucose level and a fasting blood glucose level of diabetic patients close to normal levels.

The invention further provides an antidiabetic preparation for oral administration characterized by containing nateglinide in which in a dissolution test for 1 hour, a dissolution rate of the active ingredient is at least 1% and less than 70% at pH of 1.2, 4.0 and 6.8.

The invention still further provides an antidiabetic preparation for oral administration containing nateglinide in which a dissolution rate of nateglinide is dependent on pH and in a dissolution test for 1 hour, a dissolution rate of nateglinide at pH of 1.2 is at least 20% lower than a dissolution rate thereof at pH of 6.8.

The invention furthermore provides an antidiabetic preparation for oral administration containing nateglinide in which in a dissolution test for 1 hour, a dissolution rate of the active ingredient at pH of 4.0 is less than 20% and a dissolution rate of the active ingredient at pH of 6.0 is at least 20%.

The invention moreover provides an antidiabetic preparation for oral administration containing nateglinide and at least one material selected from the group consisting of polysaccharide derivatives, polyacrylic acid derivatives, polylactic acid derivatives, polyoxyethylene derivatives, polyvinyl pyrrolidone derivatives, polyvinyl alcohol derivatives, oils and surfactants, nateglinide being dispersed in the material or being emulsified or microencapsulated with the material.

The invention moreover provides an antidiabetic preparation for oral administration containing nateglinide and at least one material selected from the group consisting of polysaccharide derivatives (except for hydroxypropylmethyl cellulose), polyacrylic acid derivatives, polylactic acid derivatives, polyvinyl pyrrolidone derivatives, polyvinyl alcohol derivatives, oils and surfactants, nateglinide being coated with the material.

BEST MODE FOR CARRYING OUT THE INVENTION

Figure 1:
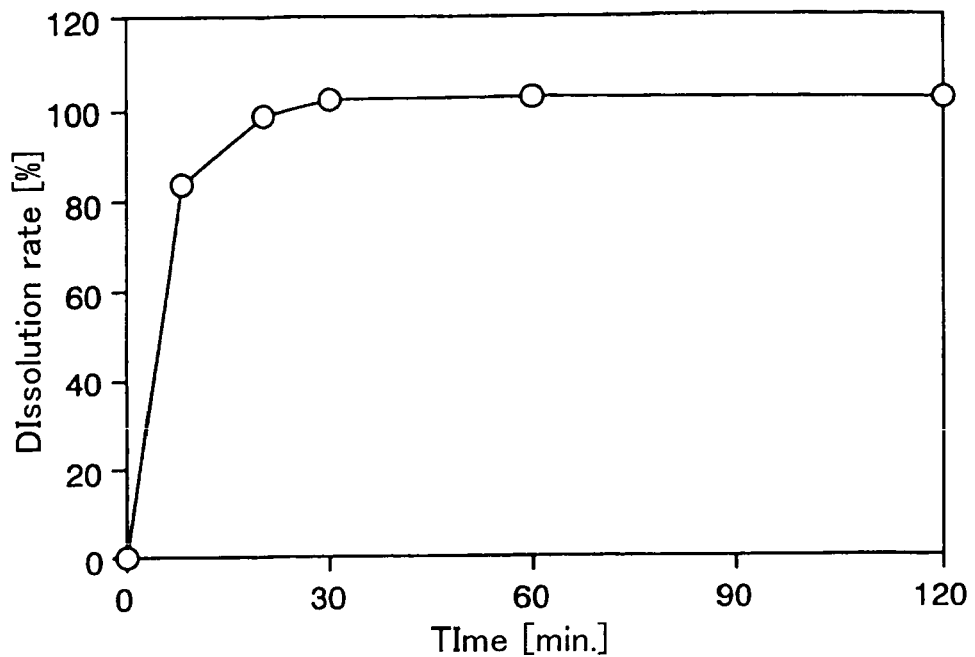
FIG. 1 is a graph showing a dissolution profile (n=3) of immediate release granules in a JP 2 solution by a puddle method (test solution 900 ml: 50 rpm) in Example 1.

In the invention, "to make both a post prandial blood glucose level and a fasting glucose level of diabetic patients close to normal levels" means that a post prandial blood glucose level and a fasting glucose level of diabetic patients are decreased to make them close to a post prandial blood glucose level and a fasting glucose level of healthy persons respectively.

Active ingredient(s) for decreasing a blood glucose level of diabetic patients may include first active ingredient(s) for decreasing a post prandial blood glucose level and second active ingredient (s) for decreasing a fasting glucose level.

In this case, the first active ingredient(s) for decreasing a post prandial blood glucose level is/are drug(s) for making a post prandial blood glucose level of diabetic patients to a blood glucose level of healthy persons. It includes drug(s), for example, a fastacting post prandial blood glucose regulator such as nateglinide or the like, and an α-glycosidase inhibitor such as acarbose or the like. Especially, nateglinide is preferable.

Further, the second active ingredient(s) for decreasing a fasting blood glucose level is/are drug(s) for making a fasting glucose level of diabetic patients to a fasting glucose level of healthy persons. It includes drug(s) or example, a sulfonylurea drug (SU drug) such as tolbutamide or the like, a biguanide drug such as metformin hydrochloride or the like, and an insulin sensitizer such as troglitazone or the like.

The invention includes a case where the preparation has both an immediate release form and a controlled release form of the active ingredient(s) or a single form of sustained release belonged to controlled release.

In this case, the active ingredient(s) for decreasing a blood glucose level may be the first active ingredient(s) used singly or the first active ingredient(s) and the second active ingredient(s) used in combination. In these cases, each of the first active ingredient(s) and the second active ingredient(s) may be single or plural.

In the invention, the single use of the first active ingredient(s) is preferable, the combined use of nateglinide and another active ingredient(s) or the single use of nateglinide are more preferable. The single use of nateglinide is especially preferable.

The "immediate release form of the active ingredient(s)" here referred to is an immediate release tablet described in Japanese Patent Laid-Open No. 194,969/1993 or various dosage forms showing its similar release behavior. Those which quickly elute a drug in the stomach after administration are included therein. Meanwhile, the "controlled release form of the active ingredient(s)" includes (i) a single form that continuously releases a drug, namely, a single form of sustained release, and (ii) a single form that releases a drug after the lapse of a fixed period of time.

Examples thereof include a pH dependent type, a time dependent type, a time limit release type, a gastrointestinal site specific release type and the like. Of these, a pH dependent type, a time dependent type and a time limit release type are preferable.

In the invention, it is especially preferable to contain a single active ingredient for decreasing a blood glucose level and have a form to continuously release the actPn ingredient from post prandial through fasting in oral administration.

As the single active ingredient for decreasing the blood glucose level here, nateglinide is preferably used.

Here, the form to continuously release the active ingredient in the invention includes a combination of an mediate release form and a controlled release form which continuously releases the active ingredient and a single form of sustained release in controlled release of the active ingredient.

The imediate release form and the controlled release form or the sustained release form of the actve ingredient(s) for decreasing the blood glucose level can easily be obtained by dispersing the active ingredient(s) for decreasing the blood glucose level in a matrix materia coating the same with a coating material, emulsifying the same with an emulsion material or microencapsulating the same with a microcapsule material. Such a method is known as a matrix method a tablet coating method, a granule coating method, an emulsion method.mcroencapsulation method or the like. Further, other methods are also available.

It is advisable that the matrix material, the coating material, the emulsion material and the microcapsule material are independently selected from the group consisting of polysaccharide derivatives, polyacrylic acid derivatives, polylactic acid derivatives, polyoxyethylene derivatives, polyvinyl pyrrolidone derivatives, polyvinyl alcohol derivatives, oils and surfactants.

The matrix method here is a method in which a drug is dispersed in the matrix material to control a release behavior. Examples of the matrix material include the foregoing polysaccharide derivatives, oils and polyacrylic acid derivatives, and the like. Any pharmaceutically acceptable compounds that form such a porous structure as to be able to diffuse a drug, water or the like in water will do.

Preferable examples thereof include cellulose derivatives, an ethyl acrylate•methyl methacrylate•chlorotrimethylammoniumethyl methacrylate copolymer, a methacrylic acid•methyl methacrylate copolymer, a methacrylic acid•ethyl acrylate copolymer, polylactic acid, a polylactic acid copolymer, polyoxyethylene, polyvinyl pyrrolidone, a 1-vinyl-2-pyrrolidone.vinyl acetate copolymer, polyvinyl alcohol, glyceride, a polyoxyethylene nonionic surfactant and a phospholipid, and these are used either singly or in admixture of two or more.

Preferable examples of cellulose derivatives here include ethyl cellulose, hydroxypropylmethyl cellulose phthalate, hydroxypropylmethyl cellulose, hydroxypropyl cellulose, hydroxypropylmethyl cellulose acetate succinate, sodium carmelose, carboxymethylethyl cellulose, cellulose acetate phthalate and hydroxyethyl cellulose, and these are used either singly or in admixture of two or more.

Further, methyl cellulose and mixtures with the foregoing compounds are also preferable.

Examples of a method of making a matrix include a high-speed agitation granulation method, a fluidized bed granulation method, a melt granulation method, a solvent removal method, a slug tableting method and the like. A method in which a drug and a matrix material can be mixed can be employed as a method of producing a matrix in the invention.

As types of a matrix, a non-erosion (non-collapsible) matrix in which a matrix structure does not collapse during release of a drug, and an erosion (collapsible) matrix in which a matrix structure collapses with release of a drug. In case of using a water-insoluble material, a non-erosion matrix is obtained. In case of using a water-soluble material, an erosion matrix is obtained.

At this time, various release behaviors can be obtained upon changing the type of the matrix material, the ratio of the matrix material and the drug or the production method. The drug release behavior is preferably a pH dependent type, a time dependent type or a time limit release type. However, the invention can be completed with other release behaviors so long as a drug can be released to make a post prandial blood glucose level and a fasting blood glucose level close to normal levels by decreasing these blood glucose levels. The specific weight ratio of the matrix material and the drug is 1:99 to 99:1, preferably 10:90 to 90:10.

The coating method includes a granule coating method and a tablet coating method. The granule coating method is a method in which core granules containing a drug are subjected to coating to control the release behavior.

As the coating material used in the coating method in the invention, for example, the foregoing polyacrylic acid derivatives, polysaccharide derivatives and oils are mentioned. Pharmaceutically acceptable compounds that form such a porous structure as to be able to diffuse a drug, water or the like in water or pharmaceutically acceptable compounds of which the solubility is dependent on pH are available. Preferable examples thereof include cellulose derivatives, an ethyl acrylate.methyl methacrylate.chlorotrimethylammonium-ethyl methacrylate copolymer, a methacrylic acid.methyl methacrylate copolymer, a methacrylic acid..ethyl acrylate copolymer, polylactic acid, a polylactic acid copolymer, polyoxyethylene, polyvinyl pyrrolidone, a 1-vinyl-2-pyrrolidone.vinyl acetate copolymer, polyvinyl alcohol, glyceride, a polyoxyethylene nonionic surfactant and a phospholipid, and these are used either singly or in admixture of two or more. As cellulose derivatives here, the same examples as listed on the matrix material are preferable.

Examples of the granule coating method include a fluidized bed coating method, a tumbling bed coating method and the like. Any method in which a coating film can be formed on core granules can be employed as the coating method in the invention.

The core granules here refer to original granules which are subjected to the coating. The core granules can be produced by a method of obtaining granules containing a drug and having a form appropriate for the coating, for example, an extrusion granulation method, a high-speed agitation granulation method, a spray drying method or the like.

The tablet coating method is a method in which core tablets containing a drug are coated. As the tablet coating method, a wet coating method or the like is mentioned. A method in which a coating film can be formed on core tablets can be employed as the coating method in the invention. The core tablets here refer to original tablets which are subjected to the coating. The core tablets can be produced by a method of obtaining tablets containing a drug and having a form appropriate for the coating, for example, a wet agglomerated granules compression method, a direct tableting method or the like.

Various release behaviors such as pH dependent release, time dependent release and the like can be obtained by changing a coating material, a coating film composition, a coating film thickness, a composition of core granules or tablets, a method of producing core granules or tablets, a coating method and the like.

The drug release behavior is preferably a pH dependent type, a time dependent type or a time limit release type. However, the invention can be completed with other release behaviors so long as a drug can be released to make a post prandial blood glucose level and a fasting blood glucose level close to normal levels by decreasing these blood glucose levels. Incidentally, examples of the pH dependent release include enteric coated granules and the like.

The emulsion method or the microencapsulation method is a method in which a drug is incorporated into an emulsion or a microcapsule to control the release behavior.

Examples of the material of the emulsion or the microcapsule include polysaccharide derivatives, polyacrylic acid derivatives, oils, surfactants and the like. Any pharmaceutically acceptable compounds that form such a structure as to control permeation of a drug from inside the emulsion or the microcapsule to the outside thereof in water will do.

Preferably, one or a admixture of two or more selected from the group consisting of cellulose derivatives, an ethyl acrylate.methyl methacrylate.chlorotrimethylammoniumethyl methacrylate copolymer, a methacrylic acid.methyl methacrylate copolymer, a methacrylic acid.ethyl acrylate copolymer, polylactic acid, a polylactic acid copolymer, polyoxyethylene, polyvinyl pyrrolidone, a 1-vinyl-2-pyrrolidone.vinyl acetate copolymer, polyvinyl alcohol, glyceride, a polyoxyethylene nonionic surfactant and a phospholipid can be used as inactive ingredient(s) material of the emulsion or the microcapsule in the invention. Preferable examples of cellulose derivatives here include ethyl cellulose, hydroxypropylmethyl cellulose phthalate, hydroxypropylmethyl cellulose, hydroxypropyl cellulose, hydroxypropylmethyl cellulose acetate succinate, sodium carmelose, carboxymethylethyl cellulose, cellulose acetate phthalate and hydroxyethyl cellulose, and these are used either singly or in admixture of two or more. Further, methyl cellulose and mixtures with the foregoing compounds are also preferable.

Examples of the emulsion method or the microencapsulation method include a submerged drying method, a phase separation method using an aqueous solution, an organic solvent or the like, a hot melt dispersion method, a spray drying method, an aerial suspension coating method, a fluidized bed coating method, a tumbling bed coating method, an interfacial polymerization method, a submerged cure-coating method and the like.

With respect to the drug release behavior, various release patterns such as pH dependent release, time dependent release and the like can be obtained by changing an inactive ingredient, a composition, a particle diameter, a production method or the like.

A pH dependent type, a time dependent type, a time limit release type are preferable. However, other release behaviors are also available so long as a drug can be released to make both a post prandial blood glucose level and a fasting blood glucose level close to normal levels by decreasing these blood glucose levels.

The second embodiment of the invention is an antidiabetic preparation for oral administration characterized in that in a dissolution test for 1 hour with one preparation containing nateglinide, the dissolution rate of the active ingredient is at least 1% and less than 70% at pH of 1.2, 4.0 and 6.8 (this embodiment corresponds to a time dependent release type of a matrix or the like, and to Examples 2, 3, 20 and 22). With respect to the dissolution test method here, in a dissolution test method by a puddle method (test solution 900 ml: 50 rpm) of Japanese Pharmacopeia 13 (hereinafter referred to as "JP"), JP disintegration test method 1st solution (JP 1 solution) containing 0.6w/v % polysorbate 80, a McIlvaine buffer solution of pH=4.0 diluted to ¼ and containing 0.5 w/v % polysorbate 80 and a JP disintegration test method 2nd solution (JP 2 solution) are used as a test solution. It is advisable that the second embodiment is conducted with a matrix, a coating, an emulsion or a microcapsule.

The third embodiment of the invention is an antidiabetic for oral administration characterized in that in one preparation containing nateglinide, a dissolution rate of nateglinide is dependent on pH and in a dissolution test for 1 hour, a dissolution rate of nateglinide at pH of 1.2 is at least 20% lower than a dissolution rate thereof at pH of 6.8. (This embodiment corresponds to a pH dependent release type, a time dependent release type and the like, and to Example 9). With respect to the dissolution test method here, in a dissolution test method by a JP puddle method (test solution 900 ml: 50 rpm), a JP disintegration test method 1st solution (pH 1.2) containing 0.6 w/v % polysorbate 80 and a JP disintegration test method 2nd solution (pH 6.8) are likewise used as a test solution. It is advisable that the third embodiment is conducted with a matrix, a coating, an emulsion or a microcapsule.

The fourth embodiment of the invention is an antidiabetic for oral administration characterized in that in a dissolution test for 1 hour with one preparation containing nateglinide, a dissolution rate of the active ingredient at pH of 4.0 is less than 20% and a dissolution rate of the active ingredient at pH of 6.0 is at least 20% (this embodiment corresponds to a pH dependent release type, and to enteric coated granules C in Example 8).

With respect to the dissolution test method here, in a dissolution test method by a JP puddle method (test solution 900 ml: 50 rpm), a McIlvaine buffer solution of pH=4.0 diluted to ¼ and containing 0.5 w/v % polysorbate 80 and a Clark-Lubs buffer solution (potassium dihydrogenphosphate-sodium hydroxide type: pH 6.0 or 6.5) are used as a test solution.

In the invention, it is further advisable that the dissolution rate of the active ingredient at pH of 6.5 is at least 60%.

The preparation having the foregoing dissolution characteristics can be obtained, as stated above, by dispersing the active ingredient for decreasing the blood glucose level in the matrix material, coating the same with the coating material, emulsifying the same with the emulsion material or microencapsulating the same with the microcapsule material.

The fifth embodiment of the invention is an antidiabetic preparation for oral administration containing nateglinide and at least one material selected from the group consisting of polysaccharide derivatives, polyacrylic acid derivatives, polylactic acid derivatives, polyoxyethylene derivatives, polyvinyl pyrrolidone derivatives, polyvinyl alcohol derivatives, oils and surfactants, nateglinide being dispersed in the material or being emulsified or microencapsulated with the material.

Further, the sixth embodiment of the invention is an antidiabetic preparation for oral administration containing nateglinide and at least one material selected from the group consisting of polysaccharide derivatives (except for hydroxypropylmethyl cellulose), polyacrylic acid derivatives, polylactic acid derivatives, polyvinyl pyrrolidone derivatives polyvinyl alcohol derivatives, oils and surfactants, nateglinide being coated with the material.

In the fifth embodiment, the material is preferably selected from ethyl cellulose, hydroxypropylmethyl cellulose phthalate, hydroxypropylmethyl cellulose acetate succinate, sodium carmelose, carboxymethylethyl cellulose, cellulose acetate phthalate, hydroxyethyl cellulose, hydroxypropylmethyl cellulose, hydroxypropyl cellulose, an ethyl acrylate.methyl methacrylate.chlorotrimethyl-ammoniumethyl methacrylate copolymer, a methacrylic acid•methyl methacrylate copolymer, a methacrylic acid•ethyl acrylate copolymer, polylactic acid, a polylactic acid copolymer, polyoxyethylene, polyvinyl pyrrolidone, a 1-vinyl-2-pyrrolidone.vinyl acetate copolymer, polyvinyl alcohol, glyceride, a polyoxyethylene nonionic surfactant and a phospholipid, these being used either singly or in admixture of two or more.

Moreover, methyl cellulose and mixtures with the foregoing compounds are also preferable.

Further, in the sixth embodiment, it is preferably selected from the group consisting of ethyl cellulose, hydroxypropylmethyl cellulose phthalate, hydroxypropylmethyl cellulose acetate succinate, sodium carmelose, carboxymethylethyl cellulose, cellulose acetate phthalate, hydroxyethyl cellulose, hydroxypropyl cellulose, an ethyl acrylate•methyl methacrylate•chlorotrimethylammoniumethyl methacrylate copolymer, a methacrylic acid•methyl methacrylate copolymer, a methacrylic acid1•ethyl acrylate copolymer, polylactic acid, a polylactic acid copolymer, polyvinyl pyrrolidone, a 1-vinyl-2-pyrrolidone•vinyl acetate copolymer, polyvinyl alcohol, glyceride, a polyoxyethylene nonionic surfactant and a phospholipid, these being used either singly or in admixture of two or more. Moreover, methyl cellulose and mixtures with the foregoing compounds are also preferable.

As the material in the fifth and sixth embodiments, hydroxypropylmethyl cellulose phthalate or a methacrylic acid.ethyl acrylate copolymer is further preferable. The methacrylic acid.ethyl acrylate copolymer here is preferably a methacrylic acid copolymer LD or a dry methacrylic acid copolymer LD. With these, nateglinide can be formed into a controlled release preparation.

The preparation for oral administration in the invention includes various forms such as granules, tablets, powders, capsules and the like.

A form of sustained release of an active ingredient for decreasing a blood glucose level alone can make both a post prandial blood glucose level and a fasting blood glucose level close to normal levels. For example, it is possible in a form satisfying the fourth embodiment.

Specifically, hydroxypropylmethyl cellulose phthalate, hydroxypropylmethyl cellulose acetate succinate, carboxymethylethyl cellulose, cellulose acetate phthalate and a methacrylic acid copolymer L can be used as the material of such a preparation. The use of hydroxypropylmethyl cellulose phthalate is especially preferable.

The combined use of an immediate release form and a controlled release form can decrease both a post prandial blood glucose level and a fasting blood glucose level with good accuracy to make them close to normal levels. A mixing ratio of a controlled release form of a drug for decreasing a post prandial blood glucose level to a normal level and an immediate release form of a drug for decreasing a post prandial blood glucose level to a normal level is 1:99 to 99:1, preferably 10:90 to 90:10 in terms of a weight ratio of a drug for decreasing a post prandial blood glucose level to make the same close to a normal level. A mixing method and a mixed form are not limited in the invention. A sustained release form can be used singly. The mixed form includes granules capsules, tablets, solutions and the like.

For example, when immediate release granules are mixed with controlled release granules, the form is granules. When these granules are encapsulated, the form is capsules. Tablets are obtained by tableting these mixed granules, tableting the respective granules in divided layers (multilayer tablet) or using a controlled release tablet formed of controlled release granules as an inner shell and immediate release granules as an outer shell and tableting them (dry coated tablet).

Further, in case of using the preparation of the invention, it can be administered at a dose of 1 mg to 10 g per day as an active ingredient, though depending on the ratio of the form for decreasing a post prandial blood glucose level to make it close to a normal level and the form for decreasing a fasting blood glucose level to make it close to a normal level and the extent of the pharmaceutical effect of the active ingredient(s).

EXAMPLES

The invention is illustrated specifically below by referring to Examples. However, these are preferable embodiments of the invention, and the invention is not limited thereto.

Designing of an Immediate Release Portion

Example 1

Immediate Release Granules

Nateglinide (375.0 g), 637.5 g of lactose monohydrate and 450.0 g of hydroxypropyl cellulose having a low degree of substitution were mixed with a high-speed agitation granulator for 10 minutes. Subsequently, 1,035 g of a binding solution of 15 g of hydroxypropyl cellulose in water was added, and granulation was conducted for 2.5 minutes. The total amount of the resulting granular product was uniformly granulated with a new speed mill, and dried with a fluidized bed drier. The obtained granules were screened through a sieve of 850 μm. The granular product remaining on the sieve of 850 μm was forcibly passed through the sieve, and both products were mixed to form immediate release granules.

The dissolution profile in the second solution of the Japanese Pharmacopeia disintegration test method was evaluated by a JP puddle method (test solution 900 ml: 50 rpm) Consequently, it was identified that almost 100% nateglinide was released in 20 minutes (FIG. 1).

Designing of A Controlled Release Portion with Matrix Granules

Example 2

Matrix Granules Using Hardened Oil (Controlled Release)

Hardened oil (1.5 g) was melted in a mortar by heating, 3 g of nateglinide was added thereto, and these were thoroughly kneaded. After the temperature was returned to room temperature, the kneaded product was granulated, and was screened to obtain matrix granules of 180 to 710 μm.

Figure 2:
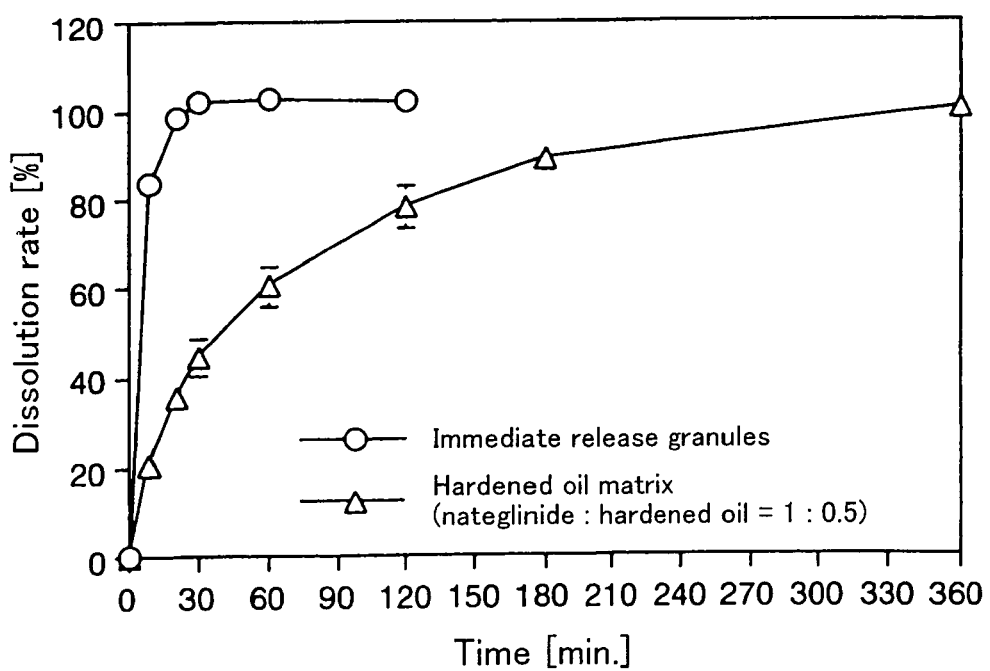
FIG. 2 is a graph showing a dissolution profile (n=3) of hardened oil (hydrogenated castor oil) matrix granules in a JP 2 solution by a puddle method (test solution 900 ml: 50 rpm) in Example 2.

The dissolution of the resulting matrix granules in the JP 2 solution was evaluated by the JP 13 puddle method (test solution 900 ml: 50 rpm) The formation of the matrix made the dissolution rate of nateglinide slower than that of immediate release granules (FIG. 2). The controlled release considered mainly effective for decreasing a fasting blood glucose level to make it close to a normal level was enabled.

Example 3

Matrix Granules Using Ethyl Cellulose (Controlled Release)

Ethyl cellulose (1.5 g) and 3.0 g of nateglinide were dissolved in ethanol, and ethanol was distilled off using an evaporator. The resulting solid matter was further vacuum-dried at 60° C. for 3 hours or more. The thus-obtained solid matter was granulated, was screened to obtain matrix granules of 180 to 710 μm.

Figure 3:
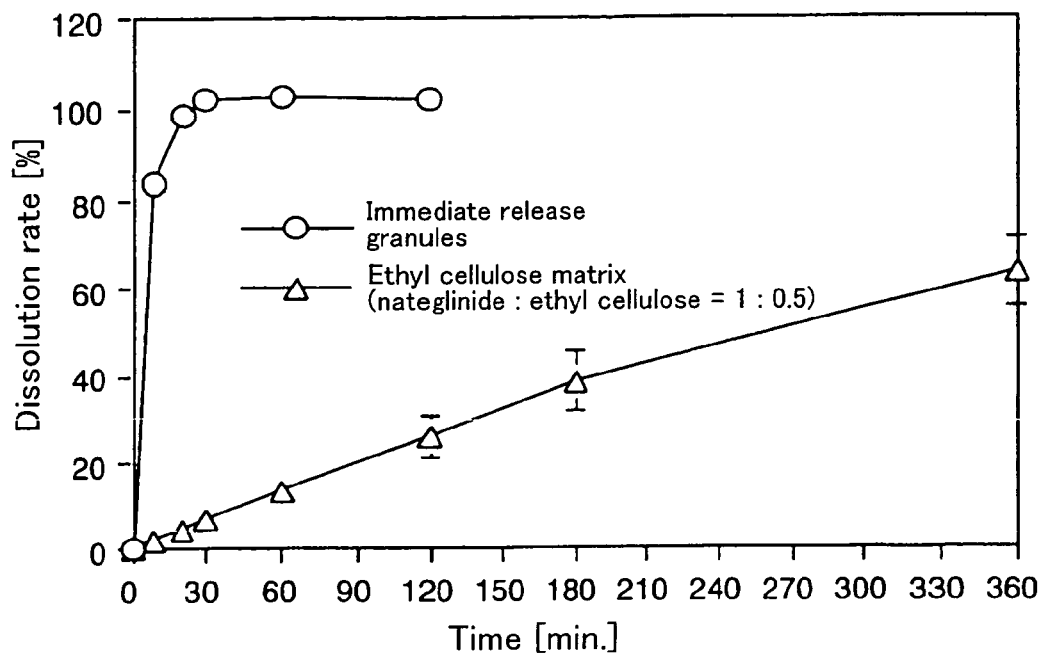
FIG. 3 is a graph showing a dissolution profile (n=3) of ethyl cellulose matrix granules in a JP 2 solution by a puddle method (test solution 900 ml: 50 rpm) in Example 3.

The dissolution of the resulting matrix granules in the JP 2 solution was evaluated by the JP 13 puddle method (test solution 900 ml: 50 rpm). The formation of the matrix made the dissolution rate of nateglinide slower than that of immediate release granules (FIG. 3). The controlled release considered mainly effective for decreasing a fasting blood glucose level to make it close to a normal level was enabled.

Example 4

Dissolution Profile when Mixing Immediate Release Granules with Controlled Release Hardened Oil Matrix Granules The dissolution profile in the JP2 solution when mixing the immediate release granules described in Example 1 with the controlled release hardened oil matrix granules described in Example 2 (2:8 nateglinide weight ratio) was evaluated by the JP 13 puddle method (test solution 900 ml: 50 rpm).

Figure 4:
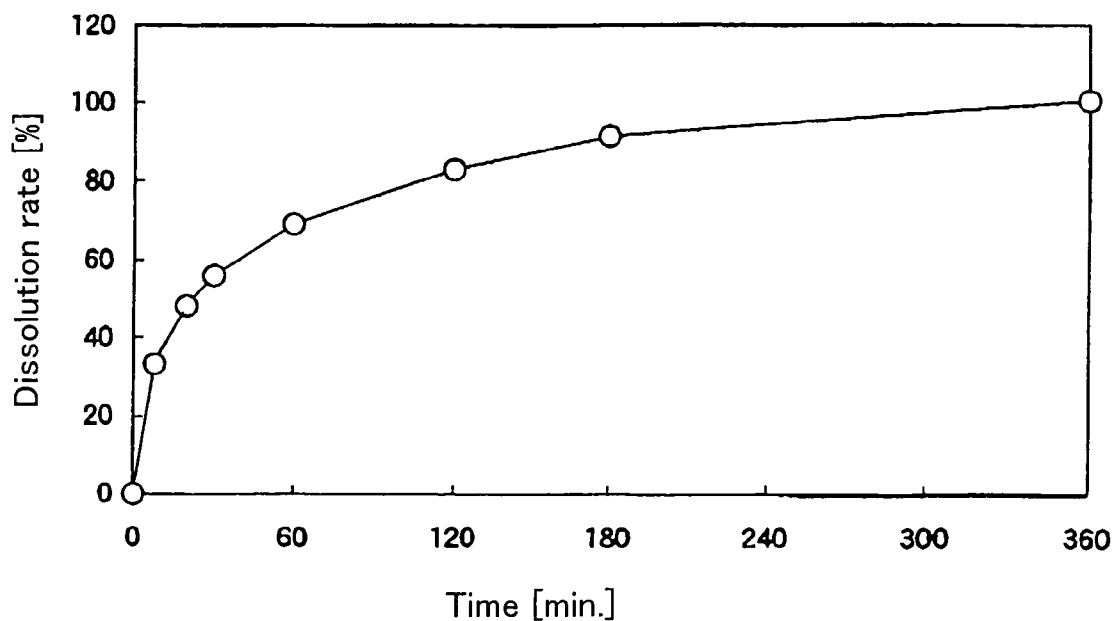
FIG. 4 is a graph showing a dissolution profile (n=3) of the mixture of immediate release granules and hardened oil matrix granules in a JP 2 solution by a puddle method (test solution 900 ml: 50 rpm) when mixing immediate release granules with hardened oil matrix granules (2:8 nateglinide weight ratio) in Example 4.

The drug was released at a rate of 65% within 60 minutes, and then gradually released over a period of 6 hours (FIG. 4).

Figure 5:
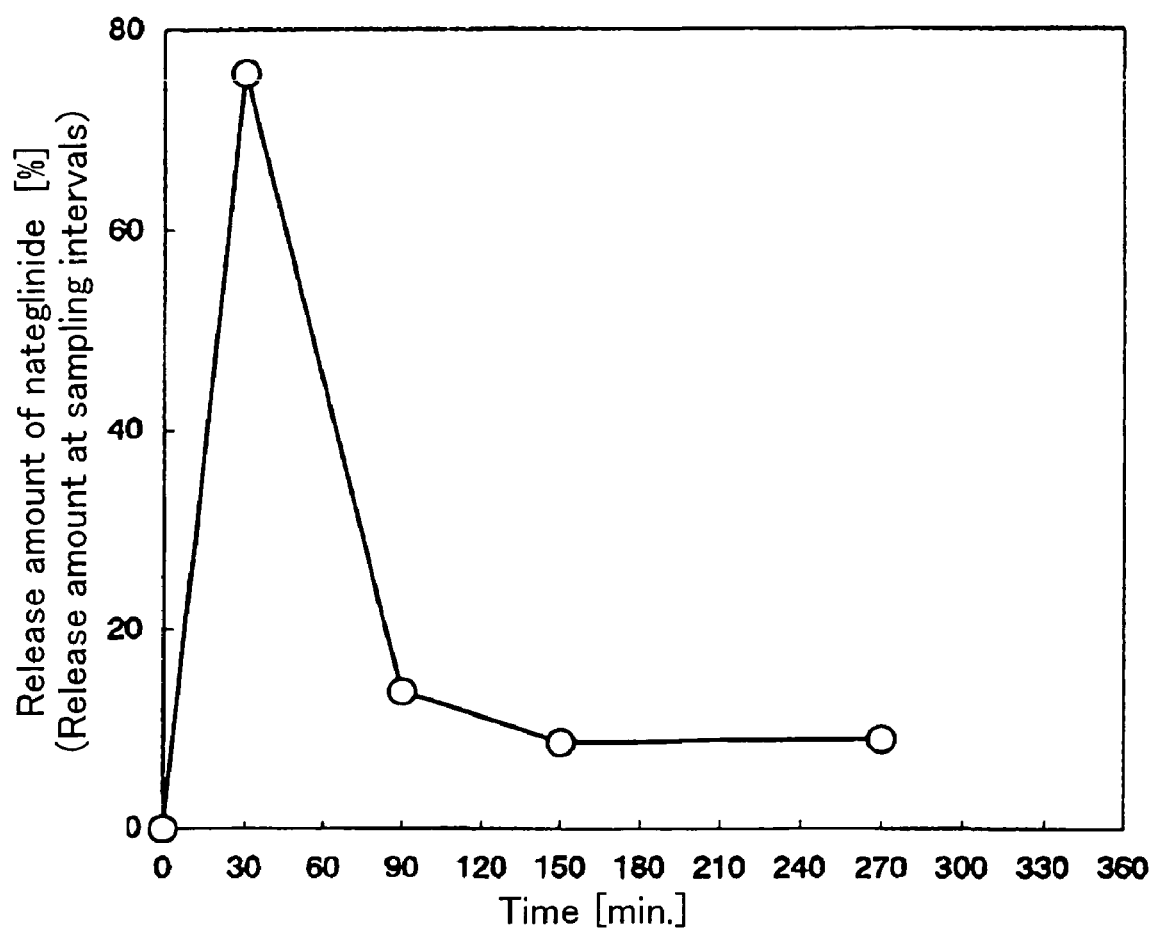
FIG. 5 is a graph showing a release amount of nateglinide (n=3) of the mixture of immediate release granules and hardened oil matrix granules in a JP 2 solution by a puddle method (test solution 900 ml: 50 rpm) when mixing immediate release granules with hardened oil matrix granules (2:8 nateglinide weight ratio) in Example 4.

The release control presumed to be effective for decreasing a post prandial blood glucose level and a fasting blood glucose level to make them close to normal levels was enabled (FIG. 5).

Designing of A Release Control Portion with Coating Granules

Example 5

Core Granules 1 for Coating

Nateglinide (250 g), 425 g of lactose monohydrate and 10 g of hydroxypropyl cellulose were suspended and dissolved in 815 g of water using a homogenizer. The suspension was then added to 300.0 g of hydroxypropyl cellulose having a low degree of substitution, and these were kneaded. The mixture was extrusion-granulated using an extrusion granulator. The resulting granular product was uniformly granulated with a marumerizer (Fuji Paudal, Q-230 model) to be spherical. Subsequently, the product was dried with a fluidized bed drier. Fractions of 850 μm to 1,400 μm were obtained by screening, and designated core granules 1 for coating.

Example 6

Core Granules 2 for Coating

Nateglinide (250 g), 425 g of lactose monohydrate and 300.0 g of hydroxypropyl cellulose having a low degree of substitution were mixed with a high-speed agitation granulator for 10 minutes. Subsequently, 690 g of a binding solution of 10 g of hydroxypropyl cellulose in water was added, and granulation was conducted for 5 minutes. Then, the product was dried with a fluidized bed drier. Fractions of 850 μm to 1,400 μm were obtained by screening, and designated core granules 2 for coating.

Example 7

Core Granules 3 for Coating

Nateglinide (250 g) and 725 g of lactose monohydrate were mixed with a high-speed agitation granulator for 10 minutes. Subsequently, 690 g of a binding solution of 10 g of hydroxypropyl cellulose in water was added, and granulation was conducted for 5 minutes. Then, the product was dried with a fluidized bed drier. Fractions of 850 μm to 1,400 μm were obtained by screening, and designated core granules 3 for coating.

Designing of a pH Dependent Release Control Portion

Example 8

Enteric Coated Granules (Controlled Release)

The coating core granules 1 described in Example 5 were subjected to enteric coating by a fluidized bed coating method. A recipe of a coating solution is shown in Tables 1 and 2 (dry methacrylic acid copolymer LD, methacrylic acid copolymer S, hydroxypropylmethyl cellulose phthalate 220824). A dry methacrylic acid copolymer LD (trade name: Eudragit L100-55, Röhm), a methacrylic acid copolymer S (trade name: Eudragit S100, Röhm) and hydroxypropylmethyl cellulose phthalate 220824 (trade name: HP-50, Shin-etsu Kagaku) were used as an enteric material.

Figure 6:
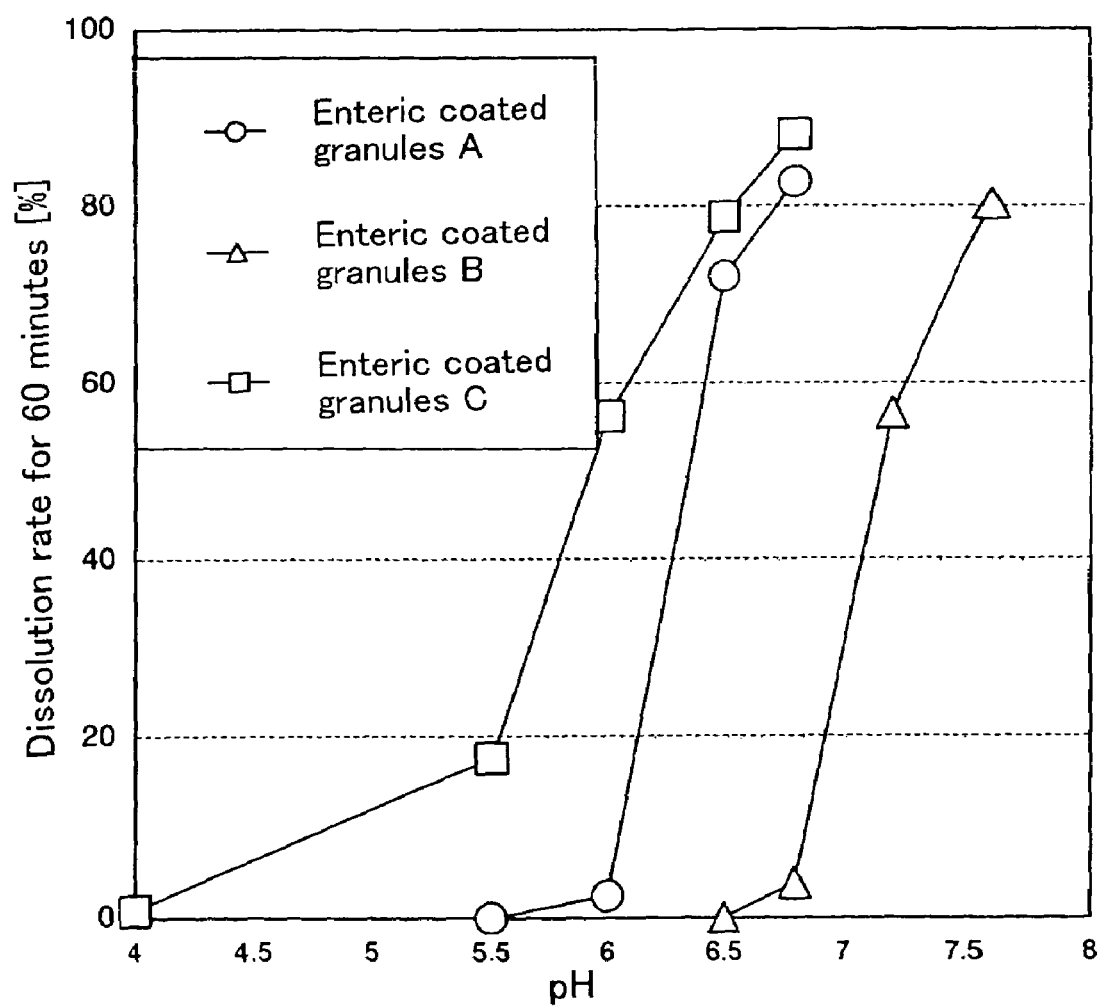
FIG. 6 is a graph showing a dissolution pH profile (n=3) of enteric coated granules A, B and C in a neutral pH region by a puddle method (test solution 900 ml: 50 rpm) in Example 8.

On enteric coated granules (enteric coated granules A, B and C respectively) obtained by coating the core granules with 33 w/w % of the dry methacrylic acid copolymer LD, 34 w/w % of the methacrylic acid copolymer S and 24 w/w % of hydroxypropylmethyl cellulose phthalate 220824, the dissolution profile in the neutral pH region (puddle method (test solution 900 ml: 50 rpm), dissolution rate for 60 minutes, Clark-Lubs buffer solution) was evaluated. It was identified that the enteric coated granules A, B and C started the dissolution at pH of 6.5, 7.2 and 5.5 (FIG. 6) respectively.

TABLE 1

| enteric material a or b | 7.0% |
|---|---|
| Macrogol 6000 | 0.7% |
| talc | 3.5% |
| ethanol | 70.0% |
| water | 18.8% | enteric material a: dry methacrylic acid copolymer LD
enteric material b: methacrylic acid copolymer S

TABLE 2

| hydroxypropylmethyl cellulose phthalate 220824 | 7.0% |
|---|---|
| Macrogol 6000 | 0.7% |
| talc | 1.0% |
| ethanol | 73.0% |
| water | 18.3% |

Example 9

Dissolution Profile when Mixing an Immediate Release Portion (Immediate Release Granules) with A Controlled Release Portion (Enteric Coated Granules)

A dissolution rate for 60 minutes (JP 13, puddle method (test solution 900 ml: 50 rpm), acidic pH: JP disintegration test method 1st solution (JP 1 solution) containing 0.6 w/v % polysorbate 80, neutral pH: Clark-Lubs buffer solution) when mixing the immediate release portion (immediate release granules) described in Example 1 with the controlled release portion (enteric coated granules A (obtained by coating the core granules with 33 w/w % of the dry metallic acid copolymer LD) (5:5 nateglinide weight ratio)) described in Example 8 was evaluated.

Figure 7:
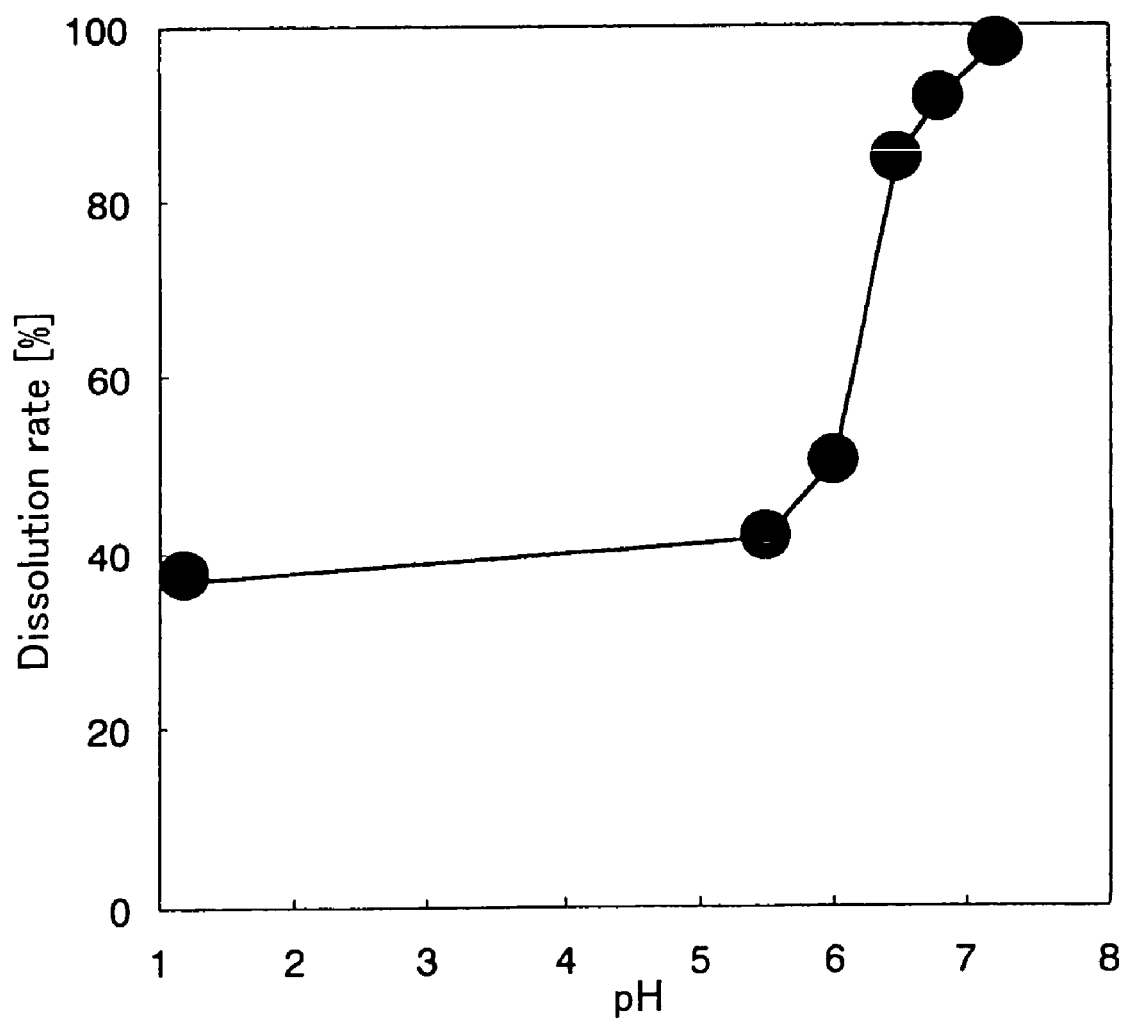
FIG. 7 is a graph showing a pH dependence (n=3) of a dissolution rate for 60 minutes by a puddle method (test solution 900 ml: 50 rpm) when mixing immediate release granules with enteric coated granules A (5:5 nateglinide weight ratio) in Example 9.

Nateglinide was dissolved from the immediate release granules alone in the range of pH=1.2 to 6.0, and nateglinide was dissolved from both the immediate release granules and the enteric coated granules at pH=6.5 or more (FIG. 7). The release control presumed to be effective for decreasing a post prandial blood glucose level and a fasting blood glucose level to make them close to normal levels was enabled.

Designing of a Time Dependent Release Portion

Example 10

Time Dependent Sustained Release Granules (Controlled Release)

The core granules 3 described in Example 7 were subjected to water-insoluble film coating by a fluidized bed coating method. A recipe of a coating solution is shown in Table 3. An aminoalkyl methacrylate copolymer RS (trade name: Eudragit RSPO, Röhm) was used as a coating material.

The dissolution profile in the JP 2 solution of granules obtained by coating the core granules with 30 w/w % of the aminoalkyl methacrylate copolymer RS was evaluated by the JP 13 puddle method (test solution 900 ml: 50 rpm). The dissolution rate of nateglinide was controlled in comparison with the immediate release granules. The release control presumed to be effective mainly for decreasing a fasting blood glucose level to make it close to a normal level was enabled.

TABLE 3

| aminoalkyl methacrylate copolymer | 7.0% |
|---|---|
| Macrogol 6000 | 0.7% |
| talc | 3.5% |
| ethanol | 70.0% |
| water | 18.8% |

Example 11

Dissolution Profile when Mixing Immediate Release Granules with Time Dependent Sustained Release Granules The dissolution profile in the JP 2 solution when mixing the immediate release granules described in Example 1 with the time dependent sustained release granules described in Example 10 (5:5 nateglinide weight ratio) was evaluated by the JP 13 puddle method (test solution 900 ml: 50 rpm). The drug was released at a rate of 50% within 30 minutes, and the drug was then gradually released over a period 6 hours. The release control presumed to be effective for decreasing a post prandial blood glucose level and a fasting blood glucose level to make them close to normal levels was enabled.

Example 12

Time Limit Release Granules (Controlled Release)

The coating core granules 1 described in Example 5 were subjected to water-insoluble film coating by a fluidized bed coating method. A recipe of a coating solution is shown in Table 3 above. An aminoalkyl methacrylate copolymer RS (trade name: Eudragit RSPO, Röhm) was used as a coating material. The dissolution profile in the JP 2 solution of granules obtained by coating the core granules with 30.0 w/w % of the aminoalkyl methacrylate copolymer RS was evaluated by the JP 13 puddle method (test solution 900 ml: 50 rpm) Nateglinide was little released from the granules till 2 hours from the start-up of the dissolution test. However, nateglinide was then rapidly released. The release control presumed to be effective mainly for decreasing a fasting blood glucose level to make it close to a normal value was enabled.

Example 13

Dissolution Profile when Mixing Immediate Release Granules with Time Limit Release Granules The dissolution profile in the JP 2 solution when mixing the immediate release granules described in Example 1 with the time limit release granules described in Example 12 (5:5 nateglinide weight ratio) was evaluated by the JP 13 puddle method (test solution 900 ml: 50 rpm). The drug was released at a rate of 50% within 30 minutes, and two hours later, the remaining drug was rapidly released. The release control presumed to be effective for decreasing a post prandial blood glucose level and a fasting blood glucose level to make them close to normal levels was enabled.

Example 14

Evaluation of Change in Blood Glucose Level by Administration of A Controlled Release Portion (Enteric Coated Granules)

Figure 8:
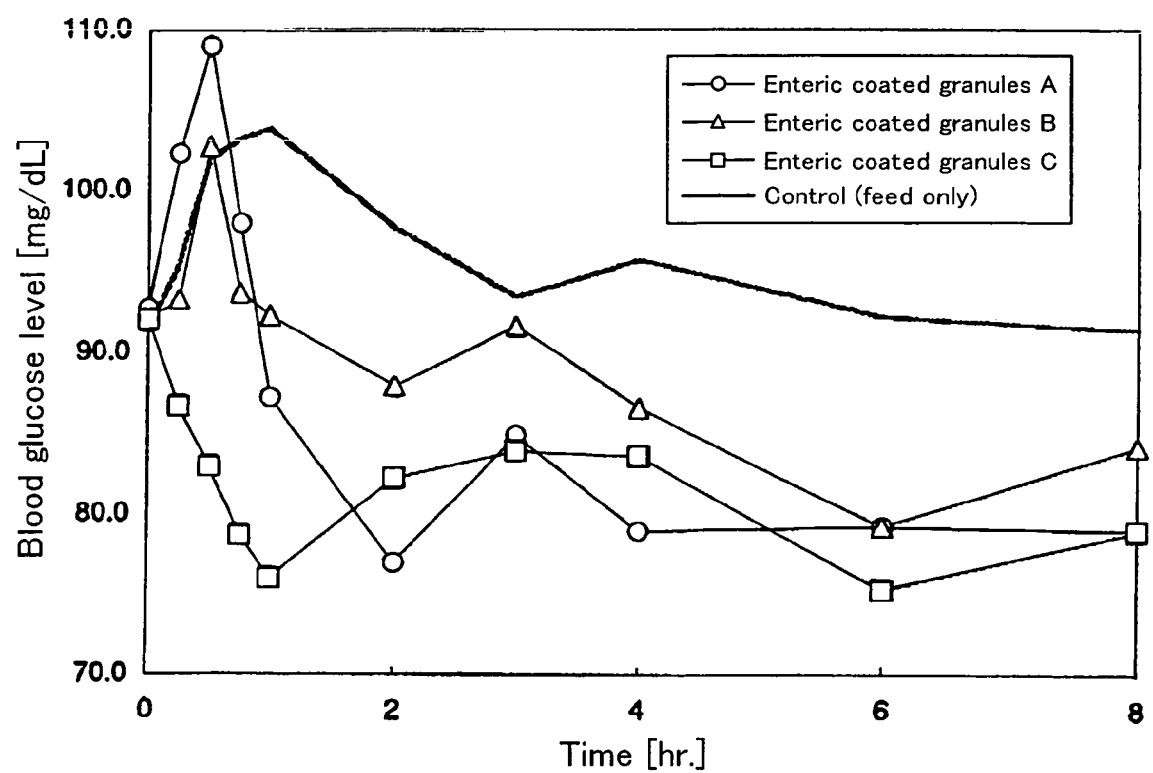
FIG. 8 is a graph showing a change in blood glucose level when administering enteric coated granules A, B and C to Beagle dogs just before feeding (nateglinide 9 mg/kg) (control: n=6, enteric coated granules: n=3) in Example 14.

The enteric coated granules A, B and C were administered as a controlled release portion to Beagle dogs just before feeding (9 mg/kg as nateglinide), and the change in blood glucose level was evaluated. Consequently, it was found that in comparison with the control (feed only), the enteric coated granules A and B decreased mainly a fasting blood glucose level and the enteric coated granules C decreased both a fasting blood glucose level and a post prandial blood glucose level to make them close to normal levels (FIG. 8).

Example 15

Evaluation of Change in Blood Glucose Level by Simultaneous Administration of an Immediate Release Portion and A Controlled Release Portion (Enteric Coated Granules)

Figure 9:
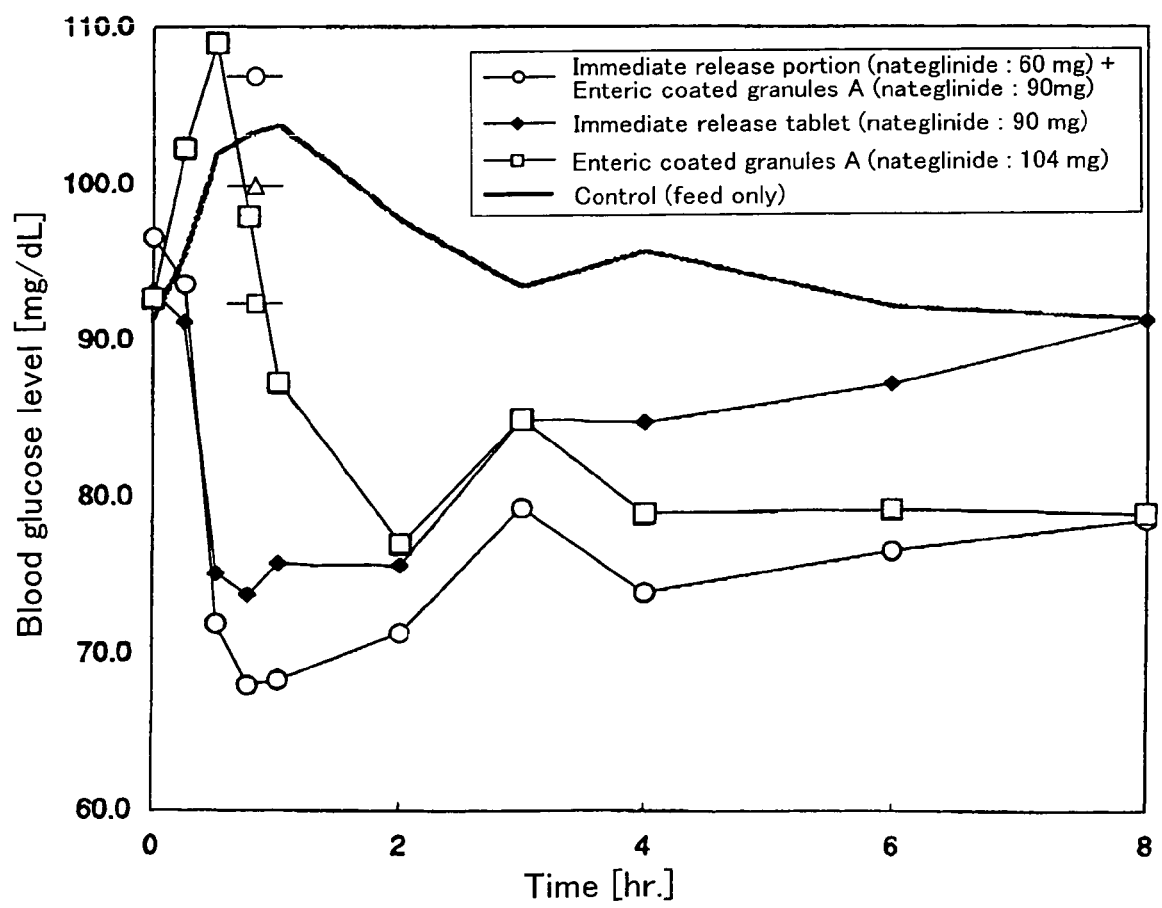
FIG. 9 is a graph showing a change in blood glucose level when administering a nateglinide preparation to Beagle dogs just before feeding (control, immediate release tablets: n=6, immediate release portion+enteric coated granules A, enteric coated granules A: n=3) in Example 15.

An immediate release portion (nateglinide: 60 mg) and enteric coated granules A (nateglinide: 90 mg) were administered to Beagle dogs just before feeding, and a change in blood glucose level was evaluated. Consequently, it was found that in comparison with the control (feed only), both a fasting blood glucose level and a post prandial blood glucose level were decreased to make them close to normal levels (FIG. 9).

Example 16

Emulsion Preparation (Controlled Release)

One gram of nateglinide, 3.0 g of soybean lecithin and 0.5 g of polyoxyethylene hardened castor oil 60 were dissolved in 60 ml of dichloromethane, and dichloromethane was distilled off with an evaporator. The resulting oil was vacuum-dried at 60° C. for 3 hours or more. The resulting oil was vigorously dispersed in 200 ml of water using a homogenizer, and then adjusted to pH of 7.5 with 0.5 mol/liter sodium hydroxide to obtain a nateglinide emulsion preparation.

Example 17

Emulsion Preparation (Controlled Release)

One gram of nateglinide, 1.0 g of corn oil and 2.0 g of polysorbate 80 were uniformly mixed. The resulting oil was vigorously dispersed in 100 ml of water using a homogenizer, and then adjusted to pH of 5.9 with a 0.5 mol/liter sodium hydroxide aqueous solution to obtain a nateglinide emulsion preparation.

Example 18

Microcapsule Preparation (Controlled Release)

Five grams of nateglinide and 15 g of polylactic acid were dissolved in dichloromethane. With vigorous stirring, this dichloromethane solution was slowly added to 1,000 ml of a 0.5 w/v % polyvinyl alcohol aqueous solution to obtain a dispersion. Dichloromethane was distilled off from the thus-obtained dispersion by a procedure at an elevated temperature under reduced pressure.

This dispersion was put in a centrifugal separator to precipitate microcapsule fractions. The supernatant was removed, and microcapsules were redispersed with the addition of water. This washing procedure was conducted twice.

The microcapsule dispersion after washing was freeze-dried to obtain a nateglinide microcapsule dispersion.

Example 19

Evaluation of Change in Blood Glucose Level by Simultaneous Administration of an Immediate Release Portion and A Controlled Release Portion (Enteric Coated Granules) (Evaluation of Dose Dependence of A Controlled Release Portion)

An immediate release portion (nateglinide: 60 mg) and enteric coated granules A (nateglinide: 60 or 90 mg) were administered to Beagle dogs just before feeding, and a change in concentration of nateglinide in plasma and a change in blood glucose level were evaluated.

Figure 10:
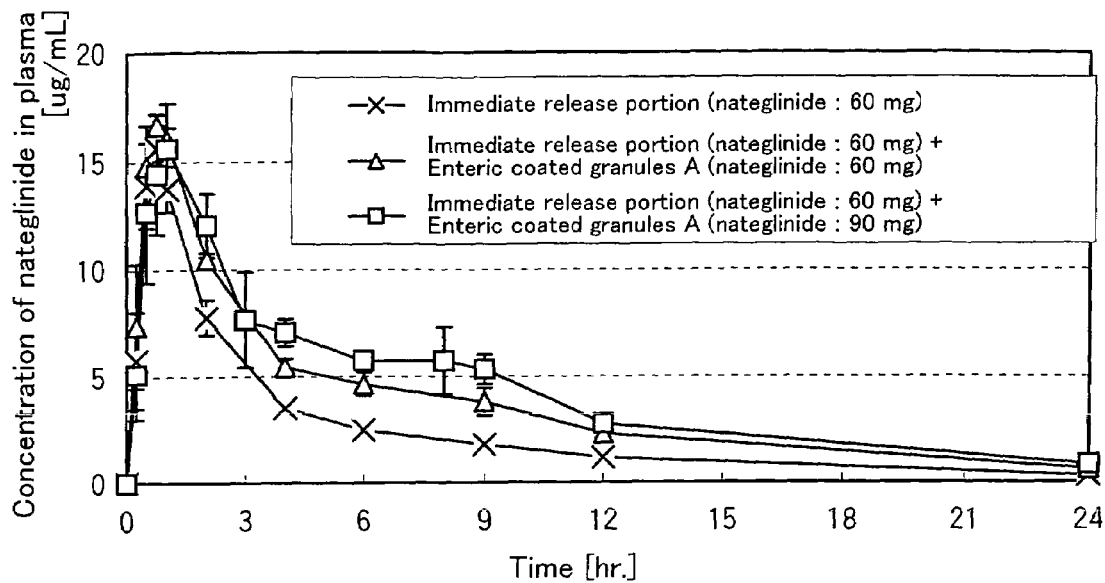
FIG. 10 is a graph showing a change in concentration of nateglinide in plasma when administering a nateglinide preparation to Beagle dogs just before feeding (average ±SE (standard error), n=6, provided n=3 at concentrations in 3, 8, 9, 12 and 24 hours on a nateglinide preparation of immediate release portion (nateglinide: 60 mg)+enteric coated granules A (nateglinide: 90 mg)) in Example 19.

In the change in concentration of nateglinide in plasma, with the increase in dose of the enteric coated granules A, Cmax (maximum concentration in plasma) was almost unchanged, whereas a tendency of the increase in concentration of nateglinide in plasma was observed in 4 to 9 hours after the administration (FIG. 10).

Figure 11:
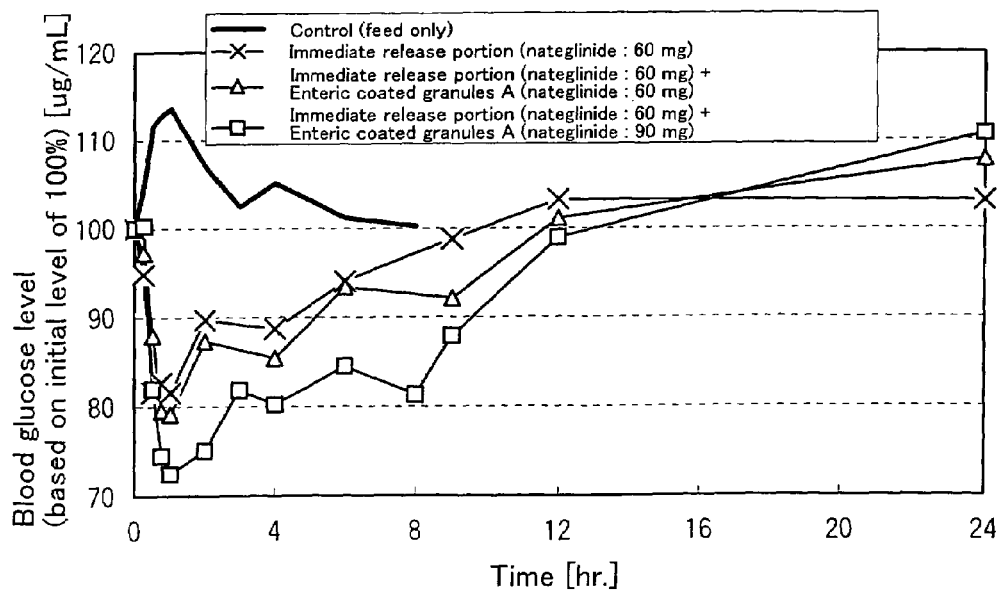
FIG. 11 is a graph showing a change in blood glucose level when a inistering a nateglinide preparation to Beagle dogs just beforefeeding (average, change in blood glucose level when a blood glucose level just before feeding is rated as 100%, n=6, provided n=3 at levels in 3, 8, 9, 12 and 24 hours on a nateglinide preparation of immediate release portion (nateglinide: 60 mg)+enteric coated granules A (nateglinide: 90 mg) in Example 19.

In the blood glucose level, with the increase in dose of the enteric coated granules A, a tendency of controlling the blood glucose level in 4 to 9 hours after the administration was observed. As in Example 15, it was found that the combination of the immediate release portion and the controlled release portion decreased both a post prandial blood glucose level and a fasting blood glucose level to make them close to normal levels, and the effect of the amount of the controlled release portion was identified as a tendency (FIG. 11).

Example 20

Erosion Matrix Tablets and Erosion Matrix Coated Tablets (Controlled Release Portion)

One hundred grams of nateglinide, 25.0 g of hydroxypropylmethyl cellulose and 41.7 g of micro-crystalline cellulose were charged in a high-speed agitation granulator, and mixed. Then, 90.0 g of water was added, and granulation was conducted for 1.5 minutes. The resulting granular product was dried on a shelf, and screened using a sieve with an opening of 850 μm. This procedure was conducted twice for mixing to obtain 317 g of the granular product.

The thus-obtained granular product was mixed with 6.47 g of magnesium stearate, and the mixture was tableted to obtain erosion matrix tablets.

The resulting erosion matrix tablets were coated using a coating solution formed by dissolving 50.0 g of hydroxypropylmethyl cellulose and 10.0 g of macrogol 6000 in 1,440 g of water (12.5% of hydroxypropylmethyl cellulose based on the weight of the erosion matrix tablet was coated) to obtain erosion matrix coated tablets.

Example 21

Dissolution Profile of Erosion Matrix Tablets and Erosion Matrix Coated Tablets

Figure 12:
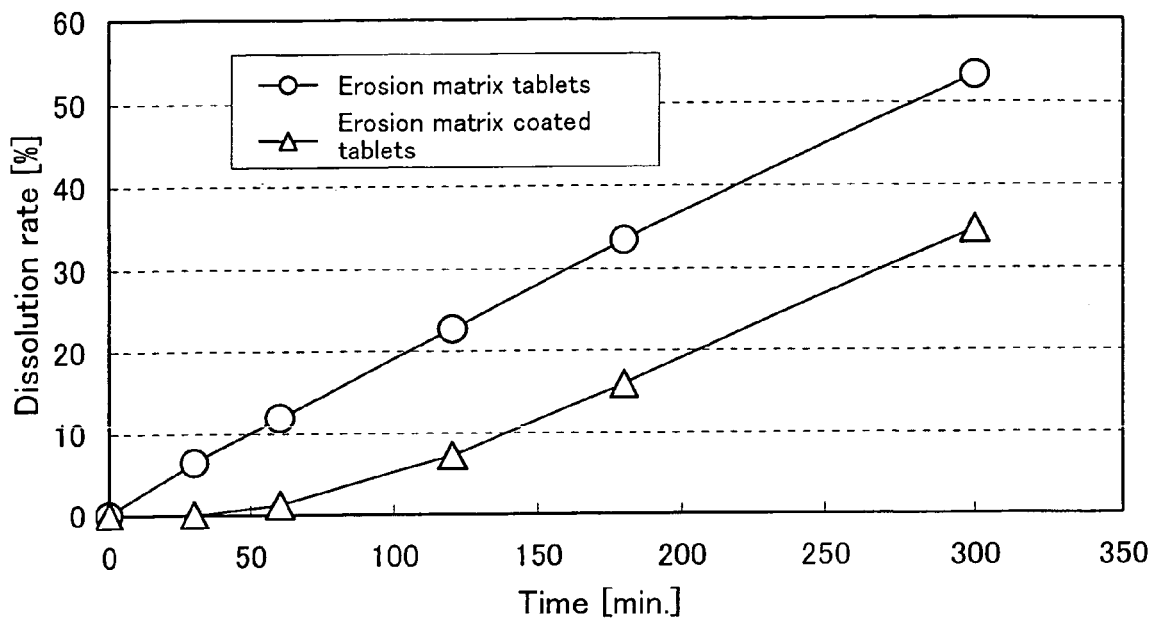
FIG. 12 is a graph showing a dissolution profile (n=3) of erosion matrix tablets and coated erosion matrix coating tablets in a JP 2 solution by a puddle method (test solution 900 ml: 50 rpm) in Example 20.

The dissolution profiles in the JP 2 solution of the erosion matrix tablets and the erosion matrix coated tablets obtained in Example 20 were evaluated by the JP 13 puddle method (test solution 900 ml: 50 rpm). The erosion matrix tablets controlled the dissolution rate of nateglinide in comparison with the immediate release granules (FIG. 12). In the erosion matrix coated tablets, a lag time of 50 minutes was observed in the dissolution in comparison with the erosion matrix tablets (FIG. 12).

The controlled release considered mainly effective for decreasing a fasting blood glucose level to make it close to a normal value was enabled.

Example 22

Dry Coated Tablets Using Erosion Matrix Tablets as an Inner Shell

Dry coated tablets were produced using the erosion matrix tablets obtained in Example 21 and the immediate release granules obtained in Example 1 (erosion matrix tablets: 153 mg, immediate release granules: 236.4 mg, magnesium stearate: 3.6 g, tablet diameter: 10 mm φ)

Example 23

Dissolution Profile of Dry Coated Tablets

Figure 13:
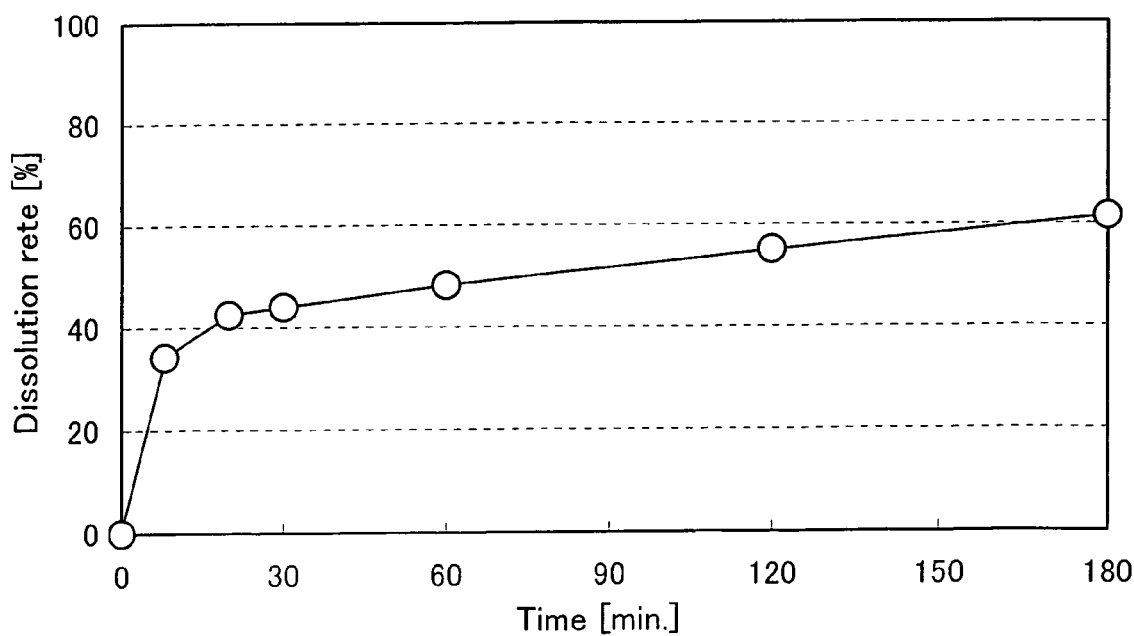
FIG. 13 is a graph showing a dissolution profile (n=3) of dry coated tablets in a JP 2 solution by a puddle method (test solution 900 ml: 50 rpm) in Example 22.

The dissolution profile in the JP 2 solution of the dry coated tablets described in Example 22 was evaluated by the JP 13 puddle method. (test solution 900 ml: 50 rpm). The drug was dissolved at a rate of 44% within 30 minutes, and then gradually released. In 3 hours, the rate reached 62% (FIG. 13). The release control presumed to be effective for decreasing a post prandial blood glucose level and a fasting blood glucose level to make them close to normal levels was enabled.

Example 24

Change in Concentration of Nateglinide of Dry Coated Tablets in Plasma and Change in Blood Glucose Level on Dogs The dry coated tablets obtained in Example 22 were administered to Beagle dogs just before feeding, and the change in concentration of nateglinide in plasma and the change in blood glucose level were evaluated.

Figure 14:
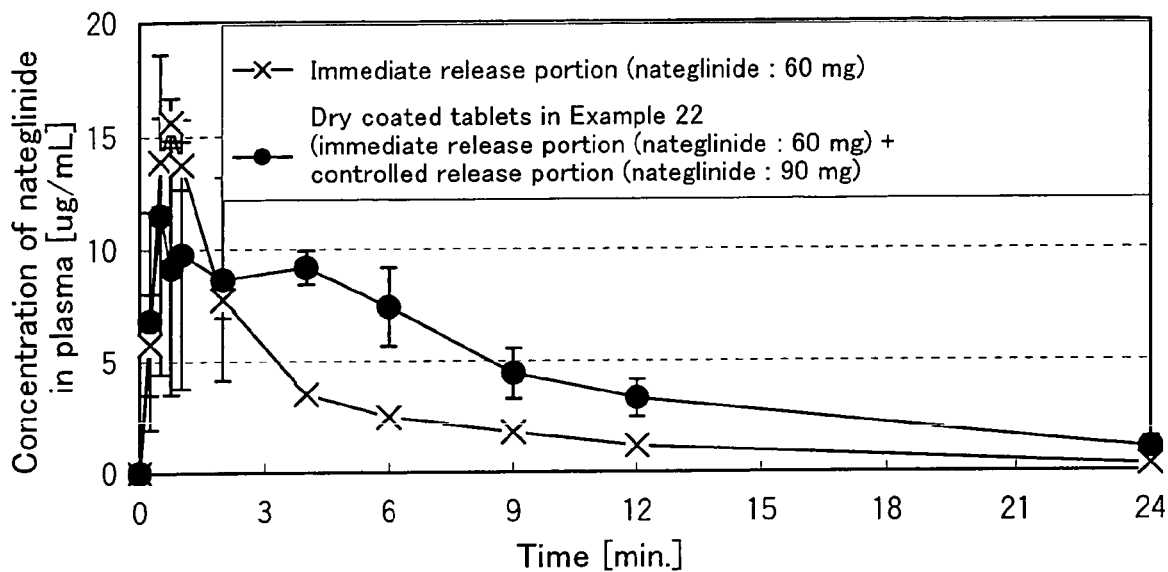
FIG. 14 is a graph showing a change in concentration of nateglinide in plasma when administering dry coated tablets to Beagle dogs just before feeding (average±SE, n=3, provided n=6 on an immediate rele se preparation (nateglinide: 60 mg) in Example 22.

In the change in concentration of nateglinide in plasma, it was found that in comparison with the immediate release preparation, Cmax was not increased so high but the concentration of nateglinide in plasma was maintained high for 9 hours after the administration (FIG. 14).

Figure 15:
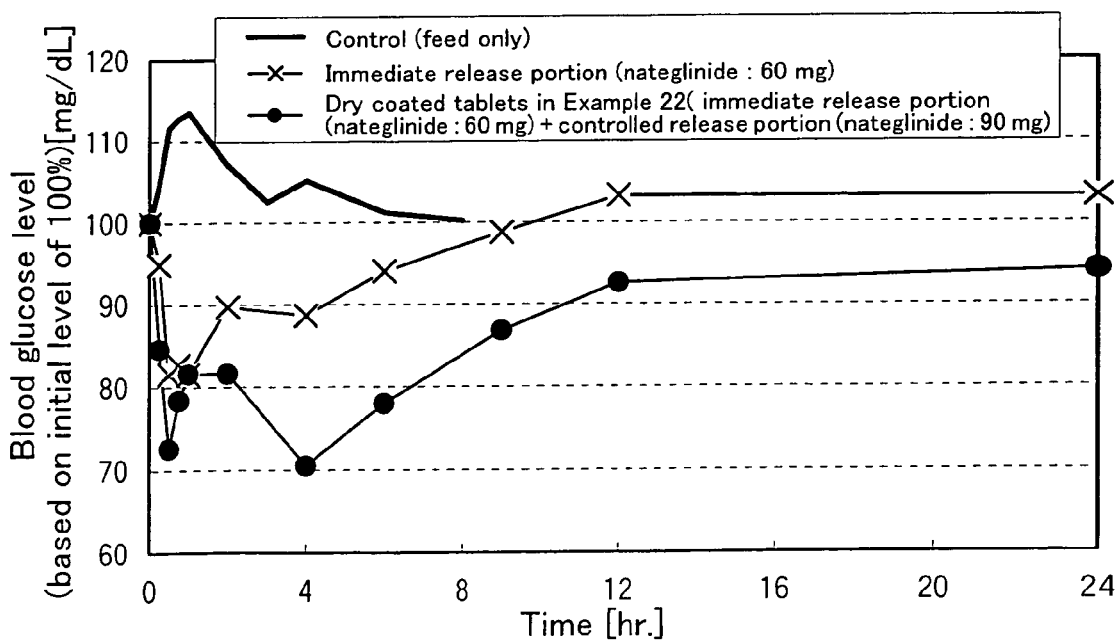
FIG. 15 is a graph showing a change in blood glucose level when administering dry coated tablets to Beagle dogs just before feeding (average, change in blood glucose level when a blood glucose level just before administration is rated as 100%, n=3, provided n=6 on a control and an immediate release preparation (nateglnide: 60 mg)) in Example 22.

With respect to the blood glucose level, it was found that both a post prandial blood glucose level and a fasting blood glucose level were decreased (FIG. 15).

According to the invention, both a post prandial blood glucose level and a fasting blood glucose level could directly be decreased with one preparation to make them close to normal levels.

Further, in the invention, one preparation provides the following advantages. (1) Even though other preparations are taken, a possibility of erroneous administration is decreased. (2) It is handy to carry. (3) There is a case where one preparation is administered before eating and another preparation after eating, and in this case, in an erroneous administration timing, no effect might be provided or a serious side effect (hypoglycemic condition) might occur. However, one preparation can avoid this possibility. (4) The costs that patients bear are decreased.

The invention claimed is:

1. A controlled release anti-diabetic preparation comprising nateglinide in an immediate release form and a controlled release form, wherein the controlled release form comprises nateglinide coated with a coating material,
wherein the preparation is in the form of a tablet, wherein said tablet comprises a controlled release inner shell comprising nateglinide dispersed in a matrix comprising a material selected from the group consisting of polysaccharide derivatives, polyacrylic acid derivatives, polyoxyethylene derivatives and polyvinyl pyrrolidone derivatives and an immediate release outer shell comprising nateglinide.

2. The preparation of claim 1, wherein the nateglinide is dispersed in a matrix comprising hydroxypropylmethyl cellulose.

3. The preparation of claim 1, wherein the nateglinide is coated with at least one entereic material selected from the group consisting of a methacrylic acid methyl methacrylate copolymer, a methacrylic acid ethyl acrylate copolymer, and hydroxypropylmethyl cellulose phthalate.

4. The preparation of claim 1, wherein said controlled release form comprises nateglinide coated with at least one enteric material selected from the group consisting of a methacrylic acid copolymer LD, a dry methacrylic acid copolymer LD, a methacrylic acid methylmethacrylate copolymer, a methacrylic acid copolymer S, hydroxypropylmethyl cellulose phthalate.

5. The preparation of claim 1, wherein the nateglinide is coated with a material selected from the group consisting of cellulose derivatives, an ethyl acrylate methyl methacrylate chlorotrimethylammoniumethyl methacrylate copolymer, a methacrylic acid methyl methacrylate copolymer, a methacrylic acid ethyl acrylate copolymer, polyoxyethylene and polyvinyl pyrrolidone.

6. The preparation of claim 1, wherein the nateglinide is coated with at least one enteric material selected from the group consisting of a methacrylic acid methyl methacrylate copolymer, a methacrylic acid ethyl acrylate copolymer, and hydroxypropylmethyl cellulose phthalate.

7. The preparation of claim 1, which further comprises at least one member selected from the group consisting of α-glycosidase inhibitors, sulfanylurea drugs, biguanide drugs, and insulin sensitizers.

8. The preparation of claim 7, which contains an α-glycosidase inhibitor.

9. The preparation of claim 8, wherein the α-glycosidase inhibitor is acarbose.

10. The preparation of claim 7, which contains a sulfonylurea drug.

11. The preparation of claim 10, wherein the sulfonylurea drug is tolbutamide.

12. The preparation of claim 7, which contains a biguanide drug.

13. The preparation of claim 12, wherein the biguanide drug is metformin.

14. The preparation of claim 7, which contains an insulin sensitizer.

15. The preparation of claim 14, wherein the insulin sensitizer is troglitazone.

16. A method of controlling both post prandial blood glucose levels and fasting blood glucose levels, comprising orally administering to a patient an effective amount of a the preparation of claim 1.

17. A method of controlling both post prandial blood glucose levels and fasting blood glucose levels, comprising orally administering to a patient an effective amount of a the preparation of claim 2.

18. A method of controlling both post prandial blood glucose levels and fasting blood glucose levels, comprising orally administering to a patient an effective amount of a the preparation of claim 3.

19. A method of controlling both post prandial blood glucose levels and fasting blood glucose levels, comprising orally administering to a patient an effective amount of a the preparation of claim 4.

20. A method of controlling both post prandial blood glucose levels and fasting blood glucose levels, comprising orally administering to a patient an effective amount of a the preparation of claim 5.

21. A method of controlling both post prandial blood glucose levels and fasting blood glucose levels, comprising orally administering to a patient an effective amount of a the preparation of claim 6.

22. A method of controlling both post prandial blood glucose levels and fasting blood glucose levels, comprising orally administering to a patient an effective amount of a the preparation of claim 7.

23. A method of controlling both post prandial blood glucose levels and fasting blood glucose levels, comprising orally administering to a patient an effective amount of the preparation of claim 8.

24. A method of controlling both post prandial blood glucose levels and fasting blood glucose levels, comprising orally administering to a patient an effective amount of the preparation of claim 9.

25. A method of controlling both post prandial blood glucose levels and fasting blood glucose levels, comprising orally administering to a patient an effective amount of the preparation of claim 10.

26. A method of controlling both post prandial blood glucose levels and fasting blood glucose levels, comprising orally administering to a patient an effective amount of the preparation of claim 11.

27. A method of controlling both post prandial blood glucose levels and fasting blood glucose levels, comprising orally administering to a patient an effective amount of the preparation of claim 12.

28. A method of controlling both post prandial blood glucose levels and fasting blood glucose levels, comprising orally administering to a patient an effective amount of the preparation of claim 13.

29. A method of controlling both post prandial blood glucose levels and fasting blood glucose levels, comprising orally administering to a patient an effective amount of the preparation of claim 14.

30. A method of controlling both post prandial blood glucose levels and fasting blood glucose levels, comprising orally administering to a patient an effective amount of the preparation of claim 15.

31. A method of treating diabetes, comprising orally administering to a patient an effective amount of the preparation of claim 1.

32. A method of treating diabetes, comprising orally administering to a patient an effective amount of the preparation of claim 2.

33. A method of treating diabetes, comprising orally administering to a patient an effective amount of the preparation of claim 3.

34. A method of treating diabetes, comprising orally administering to a patient an effective amount of the preparation of claim 4.

35. A method of treating diabetes, comprising orally administering to a patient an effective amount of the preparation of claim 5.

36. A method of treating diabetes, comprising orally administering to a patient an effective amount of the preparation of claim 6.

37. A method of treating diabetes, comprising orally administering to a patient an effective amount of the preparation of claim 7.

38. A method of treating diabetes, comprising orally administering to a patient an effective amount of the preparation of claim 8.

39. A method of treating diabetes, comprising orally administering to a patient an effective amount of the preparation of claim 9.

40. A method of treating diabetes, comprising orally administering to a patient an effective amount of the preparation of claim 10.

41. A method of treating diabetes, comprising orally administering to a patient an effective amount of the preparation of claim 11.

42. A method of treating diabetes, comprising orally administering to a patient an effective amount of the preparation of claim 12.

43. A method of treating diabetes, comprising orally administering to a patient an effective amount of the preparation of claim 13.

44. A method of treating diabetes, comprising orally administering to a patient an effective amount of the preparation of claim 14.

45. A method of treating diabetes, comprising orally administering to a patient an effective amount of the preparation of claim 15.

46. The preparation of claim 1, wherein the controlled release inner shell comprising nateglinide dispersed in a polysaccharide derivative.

47. The preparation of claim 1, wherein the controlled release inner shell comprising nateglinide dispersed in a polyacrylic acid derivative.

48. The preparation of claim 1, wherein the controlled release inner shell comprising nateglinide dispersed in a polyoxyethylene derivative.

49. The preparation of claim 1, wherein the controlled release inner shell comprising nateglinide dispersed in a polyvinyl pyrrolidone derivative.

50. A method of controlling both post prandial blood glucose levels and fasting blood glucose levels, comprising orally administering to a patient an effective amount of the preparation of claim 46.

51. A method of controlling both post prandial blood glucose levels and fasting blood glucose levels, comprising orally administering to a patient an effective amount of the preparation of claim 47.

52. A method of controlling both post prandial blood glucose levels and fasting blood glucose levels, comprising orally administering to a patient an effective amount of the preparation of claim 48.

53. A method of controlling both post prandial blood glucose levels and fasting blood glucose levels, comprising orally administering to a patient an effective amount of the preparation of claim 49.

54. A method of treating diabetes, comprising orally administering to a patient an effective amount of the preparation of claim 46.

55. A method of treating diabetes, comprising orally administering to a patient an effective amount of the preparation of claim 47.

56. A method of treating diabetes, comprising orally administering to a patient an effective amount of the preparation of claim 48.

57. A method of treating diabetes, comprising orally administering to a patient an effective amount of the preparation of claim 49.

* * * * *